United States Patent [19]

Eibl et al.

[11] Patent Number: 5,290,769
[45] Date of Patent: Mar. 1, 1994

[54] USE OF HEXADECYLPHOSPHOCHOLINE FOR THE TREATMENT OF PSORIASIS

[75] Inventors: Hansjörg Eibl, Bovenden; Clemens Unger, Göttingen; Jürgen Engel, Alzenau, all of Fed. Rep. of Germany

[73] Assignee: Asta Pharma Aktiengesellschaft, Fed. Rep. of Germany

[21] Appl. No.: 995,535

[22] Filed: Dec. 22, 1992

Related U.S. Application Data

[63] Continuation of Ser. No. 588,989, Sep. 26, 1990, abandoned.

Foreign Application Priority Data

Sep. 27, 1989 [DE] Fed. Rep. of Germany ....... 3932183

[51] Int. Cl.$^5$ .......................................... A61K 31/685
[52] U.S. Cl. .................................. 514/77; 514/863
[58] Field of Search ............................ 514/77, 863

[56] References Cited

U.S. PATENT DOCUMENTS

| | | | |
|---|---|---|---|
| 4,502,832 | 3/1985 | Becker ................................. | 415/10 |
| 4,610,979 | 9/1986 | Lautenschlager et al. ........... | 514/77 |
| 4,739,095 | 4/1988 | Eibl .................................... | 558/185 |
| 4,761,404 | 8/1988 | Bugianesi et al. ................... | 514/77 |
| 4,778,788 | 10/1988 | Munder ................................. | 514/77 |
| 4,837,023 | 6/1989 | Eibl ..................................... | 514/77 |

FOREIGN PATENT DOCUMENTS

| | | |
|---|---|---|
| 0070433 | 1/1982 | European Pat. Off. . |
| 0092190 | 4/1983 | European Pat. Off. . |
| 0208961 | 6/1986 | European Pat. Off. . |
| 0300397 | 7/1988 | European Pat. Off. . |
| 1583661 | 5/1977 | Fed. Rep. of Germany . |
| WO87/03478 | 7/1987 | PCT Int'l Appl. . |
| WO88/09662 | 12/1988 | PCT Int'l Appl. . |
| WO89/01930 | 3/1989 | PCT Int'l Appl. . |
| 2143433 | 6/1983 | United Kingdom . |

OTHER PUBLICATIONS

Chemical Abstracts 112:151889d (1990).
Chemical Abstracts vol. 111, 1989 pp. 28 and 29.
Article in 1–Pharmacology vol. 108, 1988 p. 19.

*Primary Examiner*—Leonard Schenkman
*Attorney, Agent, or Firm*—Cushman, Darby & Cushman

[57] ABSTRACT

The use of alkylphosphoric acid compounds of Formula I $$R-Y-PO_2^{\ominus}-X-R_1 \qquad \text{I}$$

where in Formula I

R represents a saturated or unsaturated hydrocarbon radical with 12 to 24 carbon atoms or where R represents the group $-CH_2-CHR_3-CH_2-Z-R_4$ and $R_3$ is a $C_1-C_6$-alkoxy group or a $C_1-C_6$-alkoxymethyl group, Z represents oxygen or sulphur and $R_4$ represents a $C_1-C_{24}$-alkyl radical, X is an oxygen atom, NH or $NR_2$ and Y is an oxygen atom or NH, $R_1$ is a $C_1-C_8$-alkyl group, or where $R_1$ represents a $C_2-C_8$-alkyl group which is unsaturated and/or substituted by halogen, amino, $C_1-C_6$-alkylamino, di-$C_1-C_6$-alkylamino, tri-$C_1-C_6$-alkylamino, hydroxy, carboxy, $C_3-C_8$-cycloalkyl or phenyl for the preparation of a pharmaceutical composition for combating psoriasis disorders.

2 Claims, No Drawings

USE OF HEXADECYLPHOSPHOCHOLINE FOR THE TREATMENT OF PSORIASIS

This is a continuation of application Ser. No. 07/588,989, filed on Sep. 26, 1990, which was abandoned upon the filing hereof.

The present invention relates to use of compounds of Formula I:

$$R-Y-PO_2^{\ominus}-X-R_1 \qquad I$$

for the treatment of psoriasis disorders.

BACKGROUND OF THE INVENTION

Alkylphosphoric acid compounds of Formula I are known substances having an anti-tumor effect.

SUMMARY OF THE INVENTION

In accordance with the present invention, it has been found that compounds of Formula I and salts thereof with physiologically acceptable acids are effective against psoriasis and related disorders.

Therefore, the present invention relates to pharmaceutical compositions which are useful for combating psoriasis disorders such as psoriasis and psoriasis related disorders and a method for the treatment of psoriasis and psoriasis related disorders which comprises administering an effective amount of such pharmaceutical compositions.

According to the invention, the term psoriasis disorders refers to skin disorders associated with hyperkeratoses, such as in particular psoriasis, Arthropathia psoriatica and parapsoriasis disorders.

Corticosteroids are currently the most frequently used treatment for psoriasis. Severe cases of psoriasis may even be treated with cytostatics (for example methotrexate). However, all these substances have pronounced and serious side effects.

In contrast, the compounds of Formula I, in the dosages used, show no or only negligible side effects. For example the effect of topical therapy with compounds of Formula I is clearly superior to that of conventional dermatological agents used in psoriasis (keratolytic agents and corticoids).

The pharmaceutical formulations of the present invention, for use in psoriasis disorders and disorders related thereto, generally contain between 1 to 1000, preferably 5 to 500 mg, in particular 10 to 100 mg per individual dose of Component I (Component I=sum of the weights of the individual compounds of Formula I) in oral, parenteral, rectal, vaginal or inhalable forms.

Should a formulation contain two or more single compounds of Formula I, these figures always apply to the total amount of compounds of Formula I (the total amount of compounds of Formula I are herein referred to as "Component I"). In an analogous manner, this applies to the following amounts which relate to Component I in connection with dosage data and their weights in the corresponding pharmaceutical formulations and to corresponding amounts in the appended claims. ("Compound I is in each case understood to refer to the single substance represented in Formula I or its physiologically acceptable salt.")

For formulations for local (topical) application to the skin and mucous membranes, the amount of Component I is for example between 0.1 mg and 1000 mg, preferably 0.1 to 500 mg.

Administration may for example be in the form of tablets, capsules, pills, coated tablets, suppositories, ointments, gels, creams, powder, dusting powder, aerosols or in liquid form. Liquid forms which may, for example, be used are: oily or alcoholic or aqueous solutions as well as suspensions and emulsions. Preferred dosage forms for application are tablets for oral administration containing between 10 and 100 mg or solutions containing between 0.01 and 10 percent by weight of Component I.

The individual dose of Component I (i.e. the total amount of compounds I) can for example lie:

a) in oral medicinal forms between 1–1000 mg, preferably 10–500 mg;

b) in parenteral medicinal forms (for example intravenous, intramuscular) between 1–1000 mg, preferably 10–500 mg;

c) in medicinal forms for inhalation (solutions or aerosols) between 1–1000 mg; preferably 10–500 mg d) in medicinal forms for rectal or vaginal application between 1–1000 mg, preferably 10–500 mg;

e) in the case of medicinal forms for local (topical) application to the skin and mucous membranes (for example in the form of solutions, lotions, emulsions, ointments and the like) between 0.1 mg 1000 mg, preferably 0.1–500 mg, the concentration of the components I (i.e. the total amount of compounds I) in such formulations being for example 0.01 to 12, in particular 0.1–8 percent by weight.

It is for example possible to recommend 1 to 3 tablets containing 1 to 100 mg of Component I (i.e. total amount I) 3 times daily or for example in the case of intravenous injection one ampoule containing 1 to 10 mg with 1 to 100 mg of Component I (i.e. total amount I) 1 to 3 times daily. In the case of oral administration the minimum daily dose is, for example, 1 mg; the maximum daily dose for oral administration should not exceed 1000 mg.

The acute toxicity of compounds I in the mouse (expressed by the $LD_{50}$ mg/kg; method after Miller and Tainter: Proc. Soc. Exper. Biol. a. med. 57 (1944) 261) is for example between 300 and 1000 mg/kg for oral application.

The pharmaceutical compositions of the invention are characterized in that they contain as active substance at least one compound of the general Formula I:

$$R-Y-PO_2^{\ominus}-X-R_1 \qquad I$$

wherein

R represents a saturated or unsaturated hydrocarbon radical with 12 to 24 carbon atoms which may also be halogen substituted, or where R represents the group $-CH_2-CHR_3-CH_2-Z-R_4$ and $R_3$ is a $C_1-C_6$-alkoxy group or a $C_1-C_6$-alkoxymethyl group, Z represents oxygen or sulphur and $R_4$ represents a $C_1-C_{24}$-alkyl radical, X is an oxygen atom, NH or $NR_2$ Y is an oxygen atom or NH, $R_1$ is a $C_1-C_8$-alkyl group or a $C_2-C_8$-alkyl group (which $C_2-C_8$-alkyl group is unsaturated and/or substituted by halogen, amino, $C_1-C_6$-alkylamino, di-$C_1-C_6$-alkylamino, tri-$C_1-C_6$-alkylamino, hydroxy, carboxy, $C_3-C_8$-cycloalkyl or phenyl, or when X is an oxygen atom, 2-tert.-butyloxycarbonylaminoethyl, 2-tert.-butyloxycarbonyl ethyl, 2,3-isopropylidendioxypropyl-(1), 2,3-dibenzyloxy-propyl-(1), 1,3-dibenzyloxy-propyl-(2) or N-$C_1$-$C_6$-alkylamino-$C_2$-$C_6$-alkyl, or, when X is the NH group, 2,3-dihydroxypropyl-(1), and $R_2$ represents a 2,3-dihydroxypropyl-(1)-group, a $C_1$-$C_8$-alkyl group or a $C_2$-$C_8$-alkyl group which is unsaturated and/or substituted by halogen, amino, $C_1$-$C_6$-alkylamino, di-$C_1$-$C_6$-alkylamino, tri-$C_1$-$C_6$-alkylamino, hydroxy, carboxy, $C_3$-$C_8$-cycloalkyl or phenyl, or a physiologically acceptable salt thereof, optionally together with conventional pharmacological additives and diluents.

The following may preferably be used as active substances: hexadecylphosphocholine, oleylphosphocholine, hexadecylphosphoric acid-(N,N)-bis-(2-chloroethyl)-amide.

Formula I also comprises possible enantiomers and diastereomers. Should the compounds be racemates, these can be split by a method which is known per se, for example using an optically active acid, in which the optically active isomers are split. Preference is, however, also given from the outset to use of enantiomeric or optionally diastereomeric starting substances, resulting in a correspondingly pure optically active or diastereomeric compound as end product.

In the context of the invention, R is preferably an alkyl group of the given chain length which is combined with the oxygen of the glycol radical via a terminal carbon atom or also via a carbon atom within the alkyl chain (for example via the carbon atom 2 or carbon atom 3 or another central carbon atom). This alkyl chain may be straight or branched. The alkyl chain R may have one, two or three carbon double bonds or triple bonds which may also be present in mixed form and/or contain halogen substituents. Halogen atoms that may be used are: fluorine, chlorine or bromine. One to three of such halogen atoms may be present in the chain R, in which case these may be located at one or at different carbon atoms of the radical R. Apart from the saturated, straight-chain alkyl radicals, preference may also be given to those with one or two carbon double bonds in the molecule. Particularly preferred are those substituents R which contain an alkyl radical with 14 to 20, preferably 15 to 20, in particular 16 to 20 carbon atoms or a corresponding alkenyl radical with 14 to 20, preferably 15 to 20, in particular 16 to 20 carbon atoms.

Examples of halogen-substituted radicals R are: chlorohexadecyl, bromohexadecyl, fluorohexadecyl, 9,10-dibromooctadecyl, 2,3-dibromooctadecyl, 15,16-dibromohexadecyl, bromotetradecyl.

Examples of unsaturated radicals R are: 9-octadecenyl radical (oleyl alcohol radical, R in Formula I represents in particular this 9-octadecenyl radical), 15hexadecenyl radical, 9,12-octadecadienyl radical (linoleyl radical).

Should more than one double or triple bond be present, these are conjugated.

Examples of saturated and unsubstituted radicals R are: tetradecyl radical, hexadecyl radical, octadecyl radical.

R preferably means, for example, the group —$CH_2$—$CHR_3$—$CH_2$—Z—$R_4$ when Y and X are oxygen and $R_1$ is a $C_1$-$C_6$-trialkylamino group (in particular trimethylamino) which is associated with X via a $C_2$-$C_3$-alkyl chain and where the positive charge of the trialkylamine cation is neutralized by the phosphoric acid anion.

The alkoxy groups $R_3$ and $R_4$ are preferably methoxy groups. The $C_1$-$C_{24}$-alkyl radical $R_4$ preferably consists of 10 to 20, in particular 12 to 18 carbon atoms and is preferably not branched.

Should $R_1$ or $R_2$ represent an unsubstituted alkyl group, this consists for example of 1-6, preferably 1-4 carbon atoms. Should $R_1$ or $R_2$ represent an unsaturated alkyl group, this consists in particular of 3 to 6 carbon atoms, it being necessary to have at least one simple C—C bond between the unsaturated function of such an unsaturated alkyl group and X. These are in particular $C_3$-$C_6$-alkenyl groups. Examples thereof are: allyl, butenyl, pentenyl, hexenyl.

Should $R_1$ or $R_2$ be substituted, this is in particular a straight chain alkyl or alkenyl radical, in this case $R_1$ preferably consists of 2-6 carbon atoms, whereby the given substituents are preferably in the -position of the alkyl or alkenyl group $R_1$ or $R_2$; this is for example the ethyl or straight propyl radical with one of the mentioned substituents in the -position (i.e. in 2-position in the case of ethyl and 3-position in the case of propyl).

Should $R_1$ be a 2-tert.-butyloxycarbonylaminoethyl radical or a 2-tert.-butyloxycarbonylethyl radical, this is preferably the D- or L-form.

Of the substituents of $R_1$ the trialkylammoniumethyl radical is preferred, in particular when X is an oxygen atom, in which case the trialkyl radicals preferably consist, in each case of one, two or three carbon atoms, preference being given to methyl groups. The trimethylammoniumethyl radical is therefore particularly preferred. In this particularly preferred embodiment the compounds of Formula I are phosphatidylcholine derivatives.

In the case of the $C_3$-$C_8$-cycloalkyl substituents, these consist in particular of 3-6 carbon atoms (for example cyclopropyl to cyclohexyl). In the case of the 2,3-dihydroxypropyl-(1)-group this is in particular the sn-1,2-dihydroxy-propylamino-(3)-structure or the sn-2,3-dihydroxypropylamino-(1)-structure.

Other examples of preferred compounds of Formula I are: oleyl-phospho-(N,N,N-trimethyl)-propanolamine, oleyl-phospho-(N,N,N-trimethyl)-butanolamine, oleyl-phospho-(N,N,N-trimethyl)-pentanolamine, oleyl-phosphoserine, oleyl-phosphoethanolamine, oleylphosphopropanolamine, oleyl-phosphobutanolamine, oleylphosphoglycerol, hexadecyl-phospho-(N,N,N-tri- methyl)-propanolamine, 1-octadecyl-2-methyl-sn-glycero-3-phosphocholine (for example ET-18-OCH$_3$, see German Patent 26 19 686) 1-Hexadecylmercapto-2-methoxymethyl-propanol-3phosphocholine (Ilmofosin).

The salts may be inner salts (for example if $R_1$ represents a trimethylammonio-alkyl group) or salts with physiologically acceptable cations. The pharmaceutical compositions of the invention or the compounds I may be present as inner salts, for example if $R_1$ contains an amino group. Should no inner salts be present, or should the radical $R_1$ contain no basic group, the negative charge of the phosphoric acid group is satisfied by a physiologically acceptable cation. Physiologically acceptable cations of this type may for example be: alkali cations (Na, K), alkaline earth cations (Mg, Ca) or the cations of organic amines, such as for example guanidinium-, morpholinium, cyclohexylammonium cation, ethylene diammonium cation, piperazonium cation (in both latter cases mono- or dibasic) or the cation derived from an amine of the formula $NR_aR_bR_c$ wherein the radicals $R_a$ to $R_c$ are the same or different and represent hydrogen, $C_1$-$C_2$-alkyl groups or oxyethyl groups.

Should cations be involved which are derived from an amine of formula $NR_aR_bR_c$, this is preferably the ammonium cation or an ammonium cation substituted by one to three $C_1$-$C_2$-alkyl groups or an ammonium cation substituted by one to three 2-hydroxyethyl groups.

The negative charge of the compounds of Formula I is thus for example saturated by a basic amino group present in the molecule or a low molecular weight mono-, di- or tri-$C_1$-$C_6$-alkylamino group or by an additional physiologically acceptable cation.

The preparation of the active substances according to the general Formula I is basically known and can for example use methods known per se or analogous methods. The basic skeleton may easily be obtained by reacting a compound of formula ROH or a functional derivative thereof with phosphorus oxychloride and triethylamine, reaction of the product with a compound $HXR_1$ and acid splitting, where R, $R_1$ and X have the above meaning.

The pharmaceutical compositions or pharmaceutical compositions of the invention contain as active substance at least one compound (component) of Formula I, optionally mixed with other pharmacologically or pharmaceutically active substances. The preparation of the pharmaceutical compositions may be carried out in conventional manner, it being possible to use known and conventional pharmaceutical auxiliary substances and other conventional carriers and diluents.

Carriers and diluents of this type that may be used are for example substances recommended or listed in the following literature references as auxiliary substances for pharmaceutical, cosmetic and related fields: Ullmanns Encyklopädie der technischen Chemie, Volume 4 (1953), page 1 to 39; Journal of Pharmaceutical Sciences, Volume 52 (1963), page 918 et seq.; H. v. Czetsch-Lindenwald, Hilfsstoffe für Pharmazie und angrenzende Gebiete; Pharm. Ind. issue 2 (1961), page 72 et seq.; Dr. H. P. Fiedler, Lexikon der Hilfsstoffe für Pharmazie, Kosmetik und angrenzende Gebiete, Cantor KG, Aulendorf in Württemberg 1981.

Examples thereof are gelatin, natural sugars such as raw sugar or lactose, lecithin, pectin, starches (for example corn starch), cyclodextrins and cyclodextrin derivatives, polyvinylpyrrolidone, polyvinyl acetate, gelatin, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated aliphatic oxyalcohols, for example methoxypropyl cellulose, methyl cellulose, hydroxypropyl-methyl cellulose, hydroxypropylmethyl cellulosephthalate); fatty acids as well as magnesium, calcium or aluminum salts of fatty acids which contain 12 to 22 carbon atoms, in particular saturated acids (for example stearates), emulsifiers, oils and fats, in particular vegetable (for example peanut oil, castor oil, olive oil, sesame oil, cottonseed oil, corn oil, wheat germ oil, sunflower seed oil, cod liver oil, in each case also hydrated; mono-, di- and triglycerides of saturated fatty acids $C_{12}H_{24}O_2$ to $C_{18}H_{36}O_2$ and their mixtures, pharmaceutically acceptable single or multivalent alcohols and polyglycols such as polyethylene glycols as well as derivatives thereof, esters of aliphatic saturated or unsaturated fatty acids (2 to 22 carbon atoms, in particular 10–18 carbon atoms) with monovalent aliphatic alcohols (1 to 20 carbon atoms) or multivalent alcohols such as glycols, glycerol, diethylene glycol, pentaerythritol, sorbitol, mannitol and the like, which may optionally also be etherified, esters of citric acid with primary alcohols, acetic acid, benzylbenzoate, dioxolanes, glycerol formals, tetrahydrofurfuryl alcohol, polyglycol ethers with $C_1$-$C_{12}$ alcohols, dimethylacetamide, lactamides, lactates, ethyl carbonates, silicones (in particular medium viscous polydimethyl siloxanes), calcium carbonate, sodium carbonate, calcium phosphate, sodium phosphate, magnesium carbonate and the like.

Other auxiliary substances that may be considered are substances promoting disintegration (so-called disintegrants) such as: cross-linked polyvinylpyrrolidone, sodium carboxy methyl starch, sodium carboxy methyl cellulose or microcrystalline cellulose. It is also possible to use known coating substances such as for example: polymerizates as well as copolymerizates of acrylic acid and/or methacrylic acid and/or their esters; copolymerizates of acrylic and methacrylic acid esters with a low ammonium group content (for example Eudragit ® RS), copolymerizates of acrylic and methacrylic acid esters and trimethylammonium methacrylate (for example Eudragit ® RL); polyvinyl acetate; fats, oils, waxes, fatty alcohols; hydroxypropylmethyl-cellulosephthalate or -acetate succinate; cellulose-, starch as well as polyvinylacetate phthalate; carboxymethyl cellulose; methylcellulosephthalate, -succinate, -phthalate succinate as well as -phthalate acid half ester; zein; ethyl cellulose as well as -succinate; shellac, gluten; ethylcarboxyethyl cellulose; ethacrylate-maleic acid anhydride-copolymer; maleic acid anhydride-vinyl methyl ether copolymer; styrolmaleic acid copolymerizate; 2-ethyl-hexyl- acrylate maleic acid anhydride; crotonic acid-vinyl acetate copolymer; glutaminic acid/glutaminic acid ester copolymer; carboxymethylethyl-cellulose glycerol monooctanoate; cellulose acetate succinate; polyarginin.

Plasticizing agents for coating substances that may be considered are:

Citric and tartaric acid esters (acetyltriethyl-, acetyltributyl-, tributyl-, triethyl citrate); glycerol and glycerol esters (glycerol diacetate; -triacetate, acetylated monoglycerides, castor oil); phthalic acid esters (dibutyl-, diamyl-, diethyl-, dimethyl-, dipropyl phthalate), D-(2-methoxy- or ethoxy ethyl)-phthalate, ethylphthalyl-, butylphthalyl ethyl- and butyl glycolate; alcohols (propylene glycol, polyethylene glycol of various chain lengths), adipates (diethyl-adipate, di(2-methoxy- or ethoxyethyl adipate); benzophenone; diethyl- and dibutylsebacate, - succinate, -tartrate; diethylene glycol dipropionate; ethylene glycol-diacetate, dibutyrate, -dipropionate; tributyl phosphate, tributyrin; polyethylene glycol sorbitane monooleate (polysorbates such as Polysorbat 80); sorbitane monooleate.

To prepare solutions or suspensions, it is for example possible to use water or physiologically acceptable organic solvents such as for example ethanol, propanol, isopropanol, 1,2-propylene glycol; glycerol-$C_1$-$C_{12}$-alkyl ethers, in particular 1-glycerol-$C_1$-$C_9$-alkyl ethers such as for example glycerol-1-n-propyl ether, glycerol-1-n-hexyl ether, glycerol-1-n-nonylether polyglycols and their derivatives, dimethylsulfoxide, fatty alcohols, triglycerides, partial esters of glycerol, paraffins and the like.

For injectable solutions or suspensions it is for example possible to use non-toxic parenterally acceptable diluents or solvents such as for example: water, 1,3-butane diol, ethanol, 1,2-propylene glycol, polyglycols in a mixture with water, Ringer's solution, isotonic sodium chloride solution or also hardened oils including synthetic mono- or diglycerides or fatty acids such as oleic acid.

Known and conventional solubilizers or emulsifiers may be used in the preparation of formulations. Solubilizers and emulsifiers that may for example be considered are: polyvinylpyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)-imidazolidone-(2). Polyoxyethylated here means that the substances in question contain polyoxyethylene chains the degree of polymerization of which generally lies between 2 and 40 and in particular between 10 and 20. Polyoxyethylated substances of this type may for example be obtained by reaction of hydroxyl group-containing compounds (for example mono- or diglycerides or unsaturated compounds such as for example those containing oleic acid radicals) with ethylene oxide (for example 40 Mol ethylene oxide per Mol glyceride.

Examples of oleotriglycerides are olive oil, peanut oil, castor oil, sesame oil, cottonseed oil, corn oil. See also Dr. H. P. Fiedler "Lexikon der Hilfsstoffe für Pharmazie, Kosmetik und angrenzende Gebiete" 1971, p. 191-195.

It is also possible to add conserving agents, stabilizers and buffer substances, for example calcium hydrogen phosphate, colloidal aluminum hydroxide, flavor enhancers, sweeteners, colorants, antioxidants and complex formers (for example ethylenediaminotetraacetic acid) and the like. It is optionally also necessary to adjust to a pH range of ca. 3 to 7 using physiologically acceptable acids or buffers to stabilize the active substance molecule. Generally speaking, as neutral to weakly acid (up to pH 5) a pH value as possible is preferred.

To prepare dermally applicable formulations it is possible to use the previously mentioned substances and spreadable or liquid hydrocarbons such as Vaseline or paraffin or gels of alkanes and polyethylene, fats and oils of plant or animal origin, which may in part also be hydrated, or synthetic fats such as glycerides of fatty acids $C_8$–$C_{18}$, as well as beeswax, cetyl palmitate, wool wax, wool wax alcohols, fatty alcohols such as cetyl alcohol, stearyl alcohol, polyethylene glycols of molecular weight 200 to 20,000; liquid waxes such as isopropyl myristate, isopropyl stearate, ethyloleate; emulsifiers such as sodium, potassium, ammonium salts of stearic acid or palmitinic acid as well as triethalolamine stearate, alkali salts of oleic acid, castor oil acid, salts of sulfurated fatty alcohols such as sodium lauryl sulphate, sodium cetyl sulphate, sodium stearyl sulphate, salts of gallic acid, sterols such as cholesterol, partial fatty acid esters of multivalent alcohols such as ethylene glycol monostearate, glycerol monostearate, pentaerythritol monostearate, partial fatty acid esters of sorbitan, partial fatty acid esters of polyoxyethylene sorbitan, sorbitol ethers of polyoxyethylene, fatty acid esters of polyoxyethylene, fatty alcohol ethers of polyoxyethylene, fatty acid esters of saccharose, fatty acid esters of polyglycerol, lecithin.

Antioxidants that may for example be used are sodium metabisulphite, ascorbic acid, gallic acid, gallic acid alkyl ester, butylhydroxyanisol, nordihydroguaiacic acid, tocopherols as well as tocopherols+synergists (substances that bind heavy metals through complex formation, for example lecithin, ascorbic acid, phosphoric acid). The addition of synergists substantially enhances the antioxygenic effect of the tocopherols.

Conserving agents that may for example be considered are sorbic acid, p-hydroxybenzoic acid esters (for example lower alkyl esters), benzoic acid, sodium benzoate, trichloroisobutyl alcohol, phenol, cresol, benzethonium chloride and formalin derivatives.

The pharmaceutical and galenic treatment of the compounds of Formula I is according to conventional standard methods. For example active substance(s) and auxiliary or carrier substances are well mixed by stirring or homogenization (for example using conventional mixing devices), working generally being at temperatures between 20° and 80° C., preferably 20° to 50° C., in particular at room temperature. Reference is made in this context to the following standard work: Sucker, Fuchs, Speiser, Pharmazeutische Technologie, Thieme Verlag Stuttgart, 1978.

Application may be to the skin or mucous membrane or to the inside of the body, for example oral, enteral, pulmonal, rectal, nasal, vaginal, lingual, intravenous, intraarterial, intracardial, intramuscular, intraperitoneal, intracutaneous, subcutaneous.

In the case of parenteral formulation forms, these are in particular sterile or sterilized products.

The concentration of compound I (Component I, i.e. the total amount) in the medicinal forms for local application is 0.01 to 12, preferably 0.05 to 10, in particular 0.1 to 8 or also 0.5 to 6 percent by weight.

For the treatment of psoriasis the compounds I (Component I) are used in particular locally, for example in the form of solutions, tinctures, suspensions, emulsions, ointments, gels, creams, pastes, lotions or shampoos. Preference is given to anhydrous formulations, facilitating the simultaneous use of salicylic acid and/or urea. Formulations of this type, which can also be made resistant to scrubbing through the addition of surfactants, are described for example in German Published Patent 36 03 859. The urea may either be present as surfactant-urea inclusion compound or also in free form. Formulations containing neither urea nor salicylic acid may of course also be used.

The concentrations of compound I used (in each case the total amount) are in this case for example 0.1 to 10% (weight/weight), preferably 0.5 to 8%, in particular 1 to 6%. The concentrations of salicylic acid used are for example 0.1 to 10%, preferably 0.2 to 8%, in particular 0.5 to 5%. The concentrations of urea used are for example 1 to 20%, preferably 3 to 18%, in particular 5 to 15%.

For topical application it has for example been found beneficial to use the compounds I (Component I) together with at least one alkyl glycerol which contains 2 to 12 carbon atoms in the alkyl radical which may be present in the form of an ether group bound to one of the primary or secondary OH groups of the glycerol. Alkyl glycerols of this type enhance or improve the effect of the compounds I. Preference is given here to alkyl glycerols with 3 to 9 carbon atoms alone or mixed.

Particularly favorable effects are thus provided by a pharmaceutical composition which contains
a) one or several compounds of Formula I (Component I) and
b) an alkyl glycerol of the general Formula II

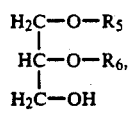

in which one of the radicals $R_5$ and $R_6$ represents an alkyl group with 2 to 12 carbon atoms and the other radical represents a hydrogen atom,
as well as optionally other conventional pharmacological additives and diluents.

Use may preferably be made of a mixture of water and an alkylglycerol mixture of nonyl or octyl glycerol, hexyl- or pentyl glycerol and propyl- or ethylglycerol. A corresponding formulation for topical use contains, for example, 1 to 100 mg of compound I (Component I, i.e. total amount I) per ml of alkyl glycerol of Formula II or of a corresponding alkylglycerol mixture with water.

A mixture of this type will hereinafter also be referred to as a cascade.

The content of Component I in mg/ml cascade is designated by a suffixed index in such a way that for example a cascade mixture containing 10 mg/ml of Component I is termed a cascade 10 and a mixture containing 60 mg of Component I per ml of cascade is referred to as cascade 60.

The preparation of alkyl glycerols is known, for example from German Published Patent 33 43 530.8. For example, alkyl glycerol-water mixtures containing for example nonyl glycerol, octyl glycerol, hexyl glycerol, pentyl glycerol, propyl glycerol and ethyl glycerol are preferred. Aqueous mixtures of this type preferably contain three of the named glycerol ethers, namely one lower (ethyl, propyl), one medium (pentyl, hexyl) and one higher (octyl, nonyl) one where the amount by weight of the lower ether is about the same as the sum of the amounts by weight of the two other glycerol ethers. The amount of water is about the same as the amount of the lower glycerol ether and is for example half the total amount of the glycerol ethers present. Examples of such glycerol ether-water mixtures are listed below:

|  | Water | Glycerol-propyl-ether | Glycerol-hexyl-ether | Glycerol-nonyl-ether |
|---|---|---|---|---|
| Parts by weight | 2 | 2 | 1 | 1 |

|  | Water | Glycerol-ethyl-ether | Glycerol-pentyl-ether | Glycerol-octyl-ether |
|---|---|---|---|---|
| Parts by weight | 2 | 2 | 1 | 1 |

Pharmaceutical compositions containing the alkyl glycerols of Formula II are particularly suitable for topical application. In order for example to treat psoriasis and disorders related thereto, the skin areas in question are for example rubbed twice to three times daily with cascade 10 to cascade 80. No harmful side effects have been observed to date.

The mode of preparation of the compounds I (Component I) in the form of the cascade (for example in the form of solutions of cascade 10 to cascade 100, in particular cascade 40 to 60) is also suitable for the preparation of suppositories for rectal insertion. Psoriasis or psoriasis disorders may be effectively treated therewith.

A particularly favorable carrier mixture for Component I consists of a mixture of about 4 parts by weight of water, 4 parts by weight of propyl glycerol and 2 parts by weight each of hexyl glycerol and nonyl glycerol.

To prepare pharmaceutical compositions containing the Component I in the presence of a glycerol ether of Formula II or a mixture of glycerol ethers of this type of Formula II, the Component I is for example used with 10,000 to 7, in particular 100 to 10, preferably 30 to 16 parts by weight (related in each case to one part by weight) of at least one glycerol ether of Formula II or a mixture of glycerol ethers of this type as well as optionally 7,700 to 0.05, in particular 400 to 2, preferably 20 to 3 parts by weight of water (also related to one part by weight of Component I, that is in each case the total amount of the compounds I). This mixing with the glycerol ethers may be carried out at the beginning of the preparation of the corresponding pharmaceutical composition, but optionally also at a later stage in the preparation.

DETAILED DESCRIPTION OF PREFERRED EMBODIMENTS

The invention is illustrated by the following examples.

EXAMPLE 1

Solution for Topical Use

Hexadecylphosphocholine solution is prepared by dissolving hexadecylphosphocholine in a solvent referred to as cascade 0.

Preparation of cascade 0

1000 g of water, 1000 g of glycerol-1-n-propyl ether, 500 g of glycerol-1-n-hexyl ether and 500 g of glycerol-1-nnonyl ether are mixed in a suitable vessel.

Preparation of the solution

About 2 liters of cascade 0 are filled into a suitable vessel and 180 g of hexadecylphosphocholine dissolved therein with stirring. The mixture is then diluted to 3 liters with cascade 0. The density of the solution is 1.003 g/ml at 26° C.

This solution is filtered under aseptic conditions in a sterile collecting vessel through a membrane filter of pore size 0.2 μm and dispensed into sterile dropping bottles of 10 ml each. Each ml of the solution contains 60 mg of hexadecylphosphocholine.

EXAMPLE 2

Capsules 50 mg Hexadecylphosphocholine hard gelatin capsules 250 g of hexadecylphosphocholine, 435.5 g of lactose monohydrate DAB 9, 241.5 g of microcrystalline cellulose DAB 9, 14 g of talcum DAB 9, 7 g of highly disperse silicon dioxide DAB 9 and 2 g of magnesium stearate DAB 9 are passed through a sieve of mesh size 0.8 mm and then homogenized in a suitable mixer for 30 mins.

190 mg batches of this capsule mass are dispensed into size 2 hard gelatin two-piece capsules in a capsule filling machine.

Each capsule contains 50 mg of hexadecylphosphocholine.

EXAMPLE 3

Tablets 100 mg hexadecylphosphocholine tablets 300 g of hexadecylphosphocholine and 600 g of lactose monohydrate DAB 9 are passed through a 0,8 mm sieve, mixed in a fluidized air bed granulating unit and granulated with 180 g of a 10% gelatin solution.

The fluidized air bed granulate, 82.8 g of microcrystalline cellulose DAB 9, 120 g of corn starch, 16.8 g of talcum and 2.4 g of magnesium stearate are passed through a sieve of 0.8 mm mesh size. This tablet mass is pressed into tablets weighing 380 mg and having a diameter of 10 mm using an appropriate tablet press.

Each tablet contains 100 mg of hexadecylphosphocholine.

EXAMPLE 4

Use of the Compounds of the Invention

The effect of the invention was tested in 6 persons who suffered from Psoriasis vulgaris. The patients had redness of the skin, crusting of the skin and scaling of the skin (over the whole body). The treatment consisted of topical application of a 6% solution of hexadecylphosphocholine in mixture of water, glycerine-propylether, glycerine-hexyl ether and glycerine-nonylether at a ratio of 2:1:1:2 by weight. Each milliliter of the glycerine, ether, water mixture contained 60 mg of the active component hexadecylphosphocholine (Kascade 60).

This solution was applied to the patients twice daily (morning and evening) for a week by dropping it onto the affected areas and massaging lightly (for example with a finger covering or a glove of polyvinyl chloride (PVC)). After one week, all patients had improved. The scaling of the lesions had diminished and the skin on the lesions had come off.

What is claimed is:

1. A method for the treatment of a psoriasis disorder which comprises administering to a host suffering from a psoriasis disorder an effective amount of hexadecylphosphocholine.

2. A method as set forth in claim 1 in which the compound is administered in combination with an alkyl glycerol of the General Formula II:

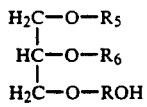

in which one of the radicals $R_5$ and $R_6$ in Formula II represents an alkyl group having 2 to 12 carbon atoms and the other radical represents a hydrogen atom, as well as optionally other conventional pharmaceutical carriers, additives and/or diluents.

* * * * *